(12) United States Patent
Bolin et al.

(10) Patent No.: US 7,037,924 B2
(45) Date of Patent: May 2, 2006

(54) GLUTAMINE FRUCTOSE-Y-PHOSPHATE AMIDOTRANSFERASE (GFAT) INHIBITORS

(75) Inventors: David Robert Bolin, Montclair, NJ (US); Shaoqing Chen, Bridgewater, NJ (US); Steven Gregory Mischke, Florham Park, NJ (US); Yimin Qian, Wayne, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 1 day.

(21) Appl. No.: 10/961,906

(22) Filed: Oct. 8, 2004

(65) Prior Publication Data

US 2005/0113407 A1    May 26, 2005

Related U.S. Application Data

(60) Provisional application No. 60/511,954, filed on Oct. 16, 2003.

(51) Int. Cl.
C07D 217/00 (2006.01)
A61K 31/47 (2006.01)

(52) U.S. Cl. .................................... 514/307; 546/146

(58) Field of Classification Search ................ 514/307; 546/146
See application file for complete search history.

(56) References Cited

U.S. PATENT DOCUMENTS 4,042,697 A    8/1977    Garside et al.

FOREIGN PATENT DOCUMENTS

FR    2.199.462    4/1974
JP    63-310813    12/1988
WO    WO 01/55117 A1    8/2001

OTHER PUBLICATIONS

Postaire et al, Bulletin de la Societe Chimique de France, vol. 6, p. 982-8, 1988.*

S.L. Bearne, J. Biol. Chem.., 271 (1996) 3052-3057.
M.A. Badet-Denisot, et. al., Bioorg. Med. Chem. Letters, 5, (1995) 815-820.
S.L. Bearne, et. al., Biochem., 34, (1995) 11515-11520.
F. Massiere, et. al., J. Amer. Chem. Soc., 119 (1997) 5748-5749.
H. Chmara, J. Gen. Microbiol., 131, (1985) 265-271.
S. Milewski, et. al., Biochim. Biophys. Acta, 1115 (1992) 225-229.
E. Anselmi, et. al., J. Pharm. Pharmacol (1992) 44(4), 337-43.
F. Markwardt, et. al., Acta Biologica et Medica Germanica (1969) 23(2), 295-306.
Chen Chen, et. al., J. Med. Chem. (2001) 44, 4001-4010.
F. Bister-Miel, et. al., Plantes Medicinales et Phytotherapie (1986), Tome XX, n° 1, p. 3-7.
E. Postaire, et. al., Ann. Pharmaceutiques Francaises (1985) 43, N°6, pp. 547-556.
D. Walterova, et . al., Collection Czechoslov. Chem. Commun, (1980), 45, pp. 956-965.
E. Taborska, et. al., Fumaflorine, a new 1-benzylisoquinoline alkaloid from *Fumaria densiflora*; Heterocycles (1997), 45(4), 817-821.

(Continued)

*Primary Examiner*—Zinna N. Davis
(74) *Attorney, Agent, or Firm*—George W. Johnston; Dennis P. Tramaloni; Samuel H. Megerditchian

(57) ABSTRACT

Compounds of formula (I) are provided,

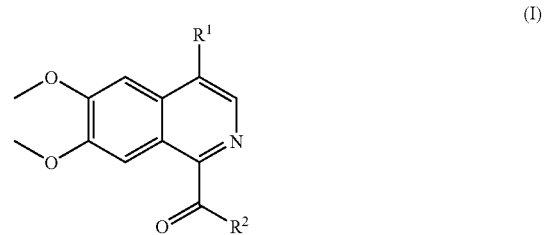

(I)

wherein $R^1$ and $R^2$ are as designated in the specification. The compounds have utility for the treatment of type 2 diabetes mellitus.

21 Claims, No Drawings

OTHER PUBLICATIONS

E. Taborska, et. al., *Fumaria densiflora* DC alkaloids; Collection of Czechoslovak Chemical Communications (1996) 61(7), 1064-1072.

E. Postaire, et. al., Vanadic oxidation of papaverine in 2.5M and 5M sulfuric acid; Bulletin de la Societe Chimique de France (1988) (6), 982-8.

M. Redrup, Analysis of the degradation products of diproteverine by moving belt LC/MS; Organic Mass Spectrometry (1989), 24(5), 309-16.

H. Ansel, et. al., Pharmaceutical Dosage Forms and Drug Delivery (6th Ed. 1995) p. 108-109.

Krogsgaard-Larsen, et. al., Textbook of Drug Design and Development (2d Ed. 1996) p. 152-191.

* cited by examiner

GLUTAMINE FRUCTOSE-Υ-PHOSPHATE AMIDOTRANSFERASE (GFAT) INHIBITORS

PRIORITY TO RELATED APPLICATIONS

This application claims the benefit of Provisional Application Ser. No. 60/511,954, filed Oct. 16, 2003.

BACKGROUND OF THE INVENTION

Diabetes is characterized by peripheral insulin resistance, increased glucose production and a decrease in the levels of insulin secretion. In general the levels of glucose in the serum are elevated. Moreover, serum glucose levels are raised for a longer period of time after ingestion of meals, and return to normal at a reduced rate. The consequences of increased glucose levels are well known, although the biochemical and molecular mechanisms underlying these phenomenon have not yet been clearly defined. Free fatty acids, triglycerides and other factors can also directly lead to increased levels of glucose.

The hexosamine pathway has been linked as one of the biochemical pathways that can contribute to insulin resistance, increased glucose production, and decreased insulin secretion. The hexosamine pathway is involved the synthesis of UDP-GlcNAc. Glucose is sequentially converted to fructose-6-phosphate, glucosamine-6-phosphate, and eventually converted to UDP-GlcNAc. Once UDP-GlcNAc is synthesized, it is incorporated into a variety of glyco-containing macromolecules, many of which are key cellular components. In addition, UDP-GlcNAc is a substrate for the enzyme OGT, O-linked GlcNAc transferase, that catalyzes the transfer of GlcNAc residues to various proteins in the cell, including cytoplasmic proteins, nuclear proteins, membrane proteins, and transcription factors. In so doing, the activity of these proteins can be significantly modulated. The rate limiting enzyme in this pathway is glutamine fructose-6-phosphate amidotransferase (GFAT), which catalyzes the amido transfer and isomerization of fructose-6-phosphate to glucosamine-6-phosphate. GFAT has been implicated in the development of diabetic symptoms, as GFAT transgenic mice are insulin resistant. The biochemical pathways that lead to insulin resistance include activation of PKC, alteration of membrane components, altered transcriptional activity, as well as other biochemical mechanisms that remain to be elucidated.

GFAT levels are elevated in type 2 diabetes mellitus (T2DM) and in rodent T2DM models. GFAT transgenic mice (muscle, liver, adipose and pancreas specific) are both insulin resistant and hyperinsulinemic. Glucosamine and products of the hexosamine pathway cause insulin resistance, increased hepatic glucose output and decreased insulin secretion. GFAT may play a role in T2DM kidney complications. GFAT is the rate limiting enzyme in the hexosamine pathway, and decreasing GFAT enzymatic activity should result in glucose lowering and be beneficial in treating diabetes.

Known classes of GFAT inhibitors are substrate-like or non-substrate-like and are believed to inhibit by either reversible or irreversible (covalent) mechanisms. The two subtrates of GFAT are the saccharide, fructose-6-phosphate, and the amino acid, glutamine. Fructose-6-phosphate-like inhibitors include: N-iodoacetylglucosamine-6-phosphate (S. L. Bearne, J. Biol. Chem., 271, 3052–3057 (1996)), and 2-amino-2-deoxyglucitol-6-phosphate (M.-A. Badet-Denisot, C. Leriche, F. Massiere, and B. Badet, Bioorg. Med. Chem. Letters, 5, 815–820 (1995)). Glutamine-like or glutamine-based inhibitors include: glutamate-γ-semialdehyde (S. L. Bearne and R. Wolfenden, Biochem., 34, 11515–11520 (1995)), L-γ-glutamyl-2-[((p-difluoromethyl)phenyl)thio]-glycine (F. Massiere, M.-A. Badet-Denisot, L. Rene, and B. Badet, J. Amer. Chem. Soc., 119, 5748–5749 (1997)), anticapsin (H. Chmara, J. Gen. Microbiol., 131, 265–271 (1985)), 6-diazo- 5-oxo-norleucine (DON), azaserine, and $N^3$-haloacetyl-L-2,3-diaminopropanoic acid (where halo=I, Br, and Cl) (S. Milewski, H. Chmara, R. Andruszkiewicz, and E. Borowski, Biochim. Biophys. Acta, 1115, 225–229 (1992)).

Papaveraldine (CA Index Name: Methanone (6,7-dimethoxy-1-isoquinolinyl) (3,4-dimethoxyphenyl)-(9C1)) exhibits properties which implicate potential usefulness in the treatment of heart disease. (Anselmi, Elsa, et al., "Selective inhibition of calcium entry induced by benzylisoquinolines in rat smooth muscle", J. Pharm. Pharmacol. (1992) 44(4), 337–43; Markwardt, Fritz, et al., "Influence of 6,7-dimethoxyisoquinoline derivatives on the function of thrombocytes", Acta Biologica et Medica Germanica (1969) 23(2), 295–306).

SUMMARY OF THE INVENTION

The present invention provides compounds of formula (I)

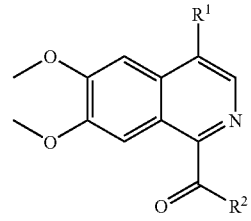

(I)

$R^1$ is —COOH, -lower alkyl-COOH, -lower alcohol, —CH$_2$OCH$_3$, —CH$_2$NH$_2$, —CH$_2$NHSO$_2$R$^7$, —C(=O)R$^8$, —CNHCH$_2$CH$_2$—R$^8$, —C(=NH)—R$^8$, —(CH$_2$)$_n$NHC(=O)R$^9$, —(CH$_2$)$_m$C(=O)N(R$^{11}$)(R$^{12}$), —C(=NH)—R$^{13}$, or —(CH$_2$)$_n$—R$^{14}$;

$R^2$ is

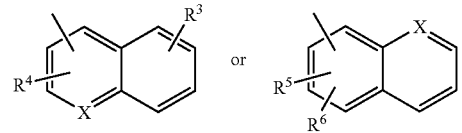

wherein

X is —CH or —N;

$R^3$, $R^4$, $R^5$, and $R^6$ are each selected from the group consisting of —H, -lower alkyl, —N(CH$_3$)$_2$, —N(CH$_3$)CH$_2$CH$_3$, —N(CH$_2$CH$_3$)CH$_2$CH$_3$, -halo, —O-lower alkene, -lower alkoxy, —O-lower alcohol, and —O(CH$_2$)$_n$-cycloalkyl; or where $R^5$ and $R^6$ are substituents on adjacent ring carbon atoms, optionally $R^5$ and $R^6$ together with the C atoms to which they are attached form a 5 or 6 membered saturated carbocyclic ring;

$R^7$ is —CF$_3$, -lower alkyl, —CH$_2$Cl, —CH$_2$CF$_3$, or —R$^8$;

$R^8$ is a 5 or 6 membered saturated substituted or unsubstituted heterocyclic ring containing one hetero atom which is selected from N, O, and S wherein the substituted ring is the heterocyclic ring substituted with —OH or -phenyl;

$R^9$ is -lower alkyl, -lower alkoxy, or —$(CH_2)_nR^{10}$;

$R^{10}$ is a 5 or 6 membered saturated or unsaturated heterocyclic ring containing one or two hetero atoms which are selected from N and O;

$R^{11}$ is —H or —$CH_3$;

$R^{12}$ is —H, -lower alkyl, —C≡N, —OH, -lower alkoxy, or —$CH_2COOCH_2CH_3$;

$R^{13}$ is -lower alkoxy, —$NH_2$ or —N-lower alkyl;

$R^{14}$ is a saturated or unsaturated 5 membered substituted or unsubstituted heterocyclic ring containing from 1 to 4 hetero atoms wherein the hetero atoms are selected from N, O and S, wherein the substituted ring is the heterocyclic ring which is substituted at one or two ring carbons with =O, or substituted at a ring N with -lower alcohol or -lower alkyl;

m is 0, 1 or 2;

n is 0 or 1;

or a pharmaceutically acceptable salt or ester thereof.

Compounds of the present invention are GFAT inhibitors which may be used to treat type II diabetes.

DETAILED DESCRIPTION OF THE INVENTION

The present invention provides compounds of formula (I)

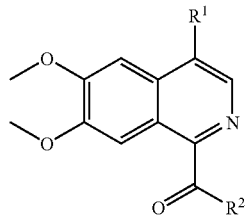

(I)

$R^1$ is —COOH, -lower alkyl-COOH, -lower alcohol, —$CH_2OCH_3$, —$CH_2NH_2$, —$CH_2NHSO_2R^7$, —C(=O)$R^8$, —CNH$CH_2CH_2$—$R^8$, —C(=NH)—$R^8$, —$(CH_2)_n$NHC(=O)$R^9$, —$(CH_2)_mC(=O)N(R^{11})(R^{12})$, —C(=NH)—$R^{13}$, or —$(CH_2)_n$—$R^{14}$;

$R^2$ is

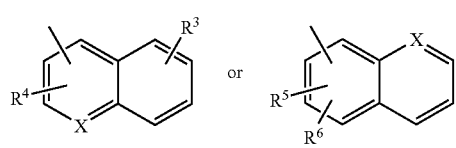

wherein

X is —CH or —N;

$R^3$, $R^4$, $R^5$, and $R^6$ are each selected from the group consisting of —H, -lower alkyl, —N(CH$_3$)$_2$, —N(CH$_3$)CH$_2$CH$_3$, —N(CH$_2$CH$_3$)CH$_2$CH$_3$, -halo, —O-lower alkene, -lower alkoxy, —O-lower alcohol, and —O(CH$_2$)$_n$-cycloalkyl; or where $R^5$ and $R^6$ are substituents on adjacent ring carbon atoms, optionally $R^5$ and $R^6$ together with the C atoms to which they are attached form a 5 or 6 membered saturated carbocyclic ring;

$R^7$ is —CF$_3$, -lower alkyl, —CH$_2$Cl, —CH$_2$CF$_3$, or —$R^8$;

$R^8$ is a 5 or 6 membered saturated substituted or unsubstituted heterocyclic ring containing one hetero atom which is selected from N, O, and S wherein the substituted ring is the heterocyclic ring substituted with —OH or -phenyl;

$R^9$ is -lower alkyl, -lower alkoxy, or —(CH$_2$)$_n$R$^{10}$;

$R^{10}$ is a 5 or 6 membered saturated or unsaturated heterocyclic ring containing one or two hetero atoms which are selected from N and O;

$R^{11}$ is —H or —CH$_3$;

$R^{12}$ is —H, -lower alkyl, —C≡N, —OH, -lower alkoxy, or —CH$_2$COOCH$_2$CH$_3$;

$R^{13}$ is -lower alkoxy, —NH$_2$ or —N-lower alkyl;

$R^{14}$ is a saturated or unsaturated 5 membered substituted or unsubstituted heterocyclic ring containing from 1 to 4 hetero atoms wherein the hetero atoms are selected from N, O and S, wherein the substituted ring is the heterocyclic ring which is substituted at one or two ring carbons with =O, or substituted at a ring N with -lower alcohol or -lower alkyl;

m is 0, 1 or 2;

n is 0 or 1;

or a pharmaceutically acceptable salt or ester thereof.

Compounds of the present invention are GFAT inhibitors which may be used to treat type II diabetes.

As used herein, the following terms set forth the scope and meaning of the various terms used to describe the invention. The term "lower" is used to mean a group consisting of one to six carbon atoms, preferably one to four carbon atoms.

"Cycloalkyl" means a non-aromatic, partially or completely saturated cyclic hydrocarbon group containing from 3 to 7 carbon atoms. Examples of cycloalkyl groups include cyclopropyl, cyclobutyl, cyclopentyl and cyclohexyl.

The term "halogen" and the term "halo" or "hetero atom", unless otherwise stated, designate all four halogens, i.e., fluorine, chlorine, bromine and iodine.

"Lower alkyl" includes both straight chain and branched chain alkyl groups having from 1 to 7 carbon atoms, preferably from 1 to 4 carbon atoms. Typical lower alkyl groups include methyl, ethyl, propyl, isopropyl, butyl, t-butyl, 2-butyl, pentyl and hexyl. When attached to another functional group, lower alkyl as used herein may be divalent, e.g., -lower alkyl-COOH.

"Lower alkoxy" means a group of the formula —O-lower alkyl, in which the term "lower alkyl" has the previously given significance. Typical lower alkoxy groups include methoxy, ethoxy, propoxy, isopropoxy, n-butoxy, isobutoxy, sec. butoxy, and tert.butoxy.

"Lower alcohol" means a -lower alkyl where at least one of the hydrogens is replaced by a hydroxy, at any site including the end. Typical lower alcohol groups include ethanol, isopropanol, and n-propanol.

"Lower alkene" means a -lower alkyl having at least 3 C atoms, where at least one of the bonds between two carbon atoms starting from at least the second carbon of the -lower alkyl has a double bond and at least one H atom on each of these C's is not present. The lower alkene is thus at least partially unsaturated. Typical lower alkenes include 2-propene, 3-methyl-2-butene, and 2,3-dimethyl-2-butene.

"Aryl" signifies a phenyl group. Where indicated herein, aryl may be substituted in one or more positions with a designated substituent or substituents.

"Heteroaryl" means a 5 or 6 membered saturated heterocyclic ring containing at least one hetero atom selected from N, O and S. Where indicated herein, heteroaryl may be substituted in one or more positions with a designated substituent or substituents.

"IC$_{50}$" refers to the concentration of a particular compound of the present invention required to inhibit 50% of in vitro GFAT activity measured as indicated herein.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to whom the particular compound is administered.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. In the present invention, esters may be present, for example, where $R^1$ is —COOH or -lower alkyl-COOH. Examples of ester groups which are cleaved (in this case hydrolyzed) in vivo to the corresponding carboxylic acids are those in which the cleaved hydrogen is replaced with -lower alkyl which is optionally substituted with heterocycle, cycloalkyl, etc. Examples of substituted lower alkyl esters are those in which -lower alkyl is substituted with pyrrolidine, piperidine, morpholine, N-methylpiperazine, etc.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

The present application incorporates by reference in its entirety U.S. Provisional Application No. 60/471,690 filed on May 19, 2003, entitled Glutamine Fructose-y-Phosphate Amedotransferase (GFAT) Inhibitors.

The present invention also provides pharmaceutical compositions comprising at least one compound of formula I, or a pharmaceutically acceptable salt thereof, and a pharmaceutically acceptable carrier.

The pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, stearic acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. In such case, the pharmaceutically acceptable carrier is deemed to be the soft gelatin capsule. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The compounds of the present invention are useful as medicaments for the treatment of type II diabetes. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 1,000 mg per day should be appropriate, although the upper limit may be exceeded when indicated. The daily dosage can be administered as a single dose or in divided doses, or for parenteral administration, it may be given as continuous infusion.

The compounds of the present invention may be made as indicated or in accordance with methodologies known to those of skill in the art.

General Synthetic Schemes

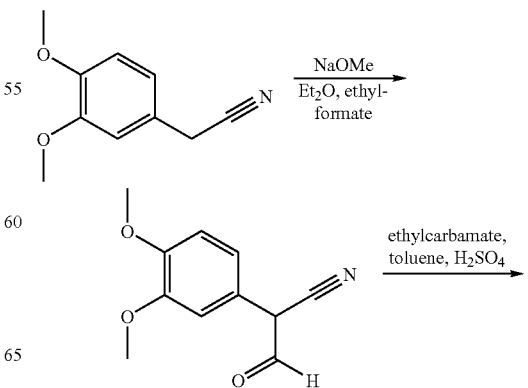

-continued
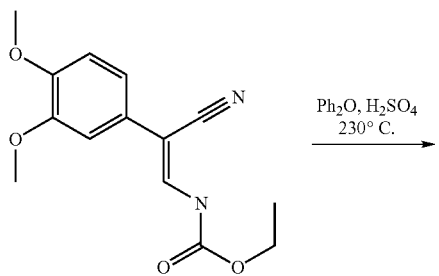
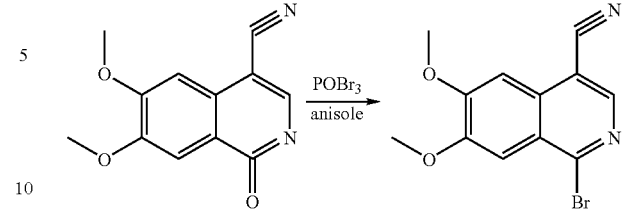
Scheme 2
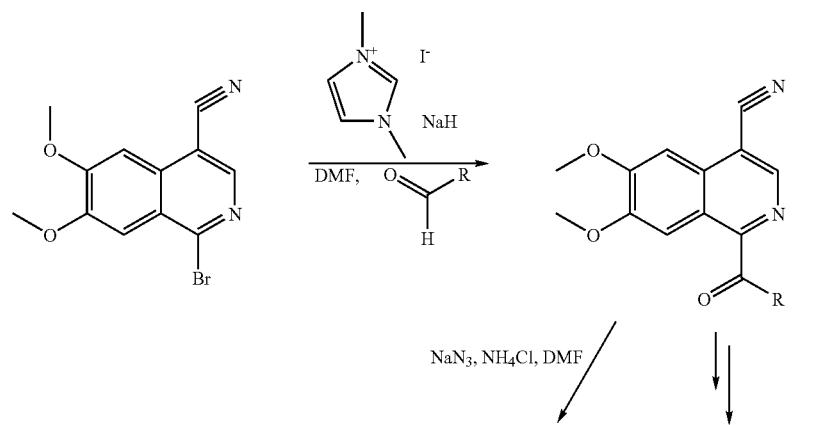
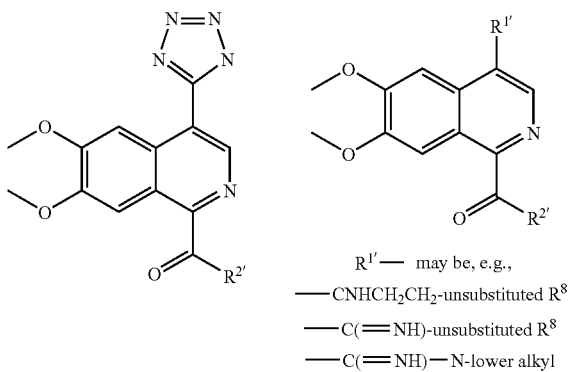
R[1'] — may be, e.g.,
—CNHCH$_2$CH$_2$-unsubstituted R[8]
—C(═NH)-unsubstituted R[8]
—C(═NH)—N-lower alkyl
R[2'] — may be, e.g.,
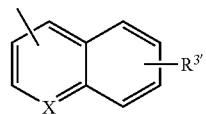 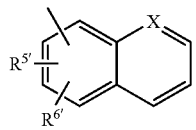 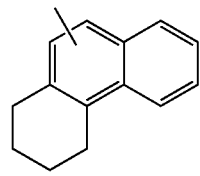
X, R[3'], R[5'] and R[6'] may be, e.g.,
X—CH, N
R[3']—H, CH$_3$
R[5']—H, OCH$_3$, OCH$_2$CH═CH$_2$
R[6']—H, OCH$_3$, N(CH$_3$)$_2$, CH$_3$

US 7,037,924 B2

9

Scheme 3

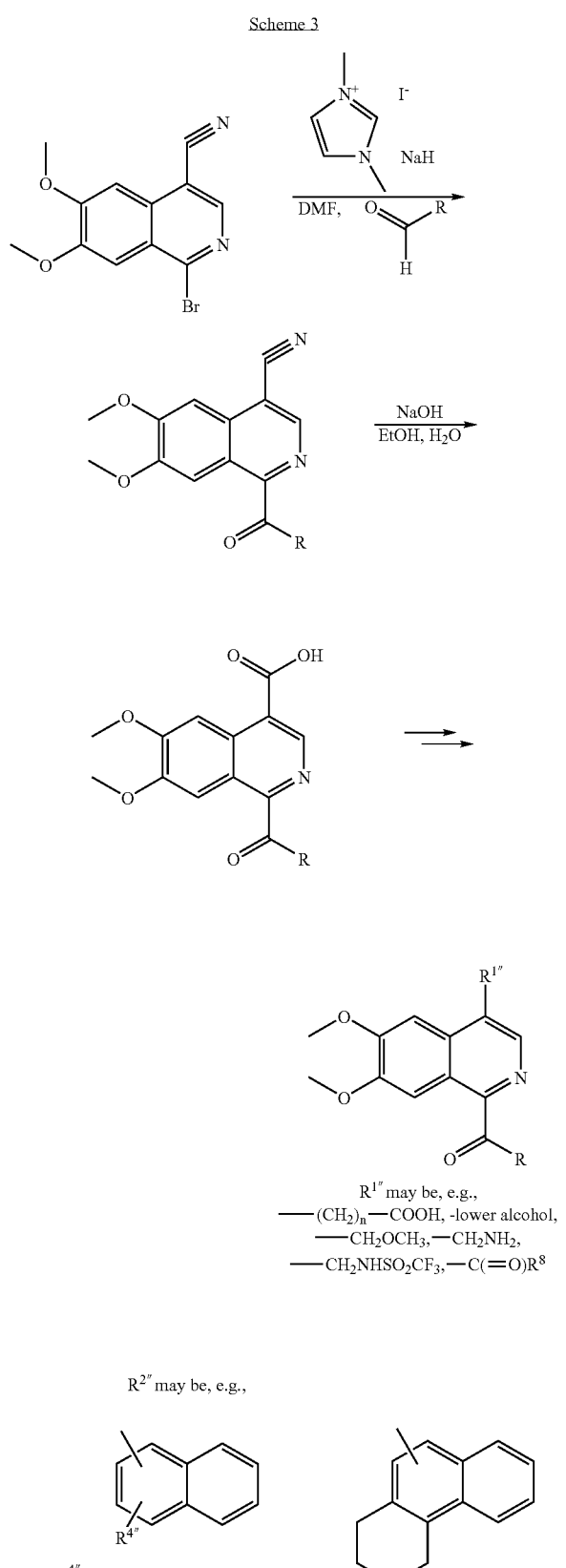

R¹" may be, e.g.,
—(CH₂)ₙ—COOH, -lower alcohol,
—CH₂OCH₃, —CH₂NH₂,
—CH₂NHSO₂CF₃, —C(=O)R⁸

R²" may be, e.g.,

R⁴" may be, e.g., H, OCH₃, N(CH₃)₂

10

EXAMPLE 1

(Naphthalen-2-yl)-[6,7-dimethoxy-4-(1H-tetrazol-5-yl)-isoquinolin-1-yl]-methanone, trifluoroacetic acid salt To the mixture of homoveratronitrile (17.7 g, 0.1 mol) and sodium methoxide (7.7 g, 0.11 mol) in ether (300 mL) was added the solution of ethyl formate (8.2 mL) in ether (100 mL). The mixture was stirred vigorously for 3 days. The precipitated solid was filtered, washed with ether. The solid was dissolved in water (100 mL). After adding 10% acetic acid to pH=3, the resulting precipitation was collected by filtration, washed with water and dried to afford 2-(3,4-dimethoxy phenyl)-3-oxo-propionitrile as white solid (19 g, 93%). LC-MS m/e calcd for $C_{11}H_{11}NO_3$ (MH⁺) 206. found 206.

To the mixture of 2-(3,4-dimethoxy-phenyl)-3-oxo-propionitrile (20.5 g, 0.1 mol), urethane (8.9 g, 0.1 mol) in toluene (400 mL) was added concentrated sulfuric acid (0.5 mL, 10 mmol). The mixture was refluxed and was concentrated by slow distillation to a volume to about 50 mL. The cooled mixture was filtered and the precipitate was washed with benzene and dried. Flash chromatography (Merck Silica gel 60, 70–230 mesh, 20% methylenechloride) afforded [2-cyano-2-(3,4-dimethoxy-phenyl)-vinyl]-carbamic acid ethyl ester as a solid: LC-MS m/e calcd for $C_{14}H_{16}N_2O_4$ (MH⁺) 277. found 277. ¹H NMR (300 MHz) compatible.

Concentrated sulfuric acid (0.4 mL) was added the the mixture of [2-cyano-2-(3,4-dimethoxy-phenyl)-vinyl]-carbamic acid ethyl ester (33.5 g, 121 mmol) and diphenyl ether (230 mL). The mixture was heated to 230° C. for 6 hr. After cooling, ether was added to precipitate the solid. The resulting solid was collected by filtration, washed with ether and dried to afford 6,7-dimethoxy-1-oxo-1,2-dihydro-isoquinoline-4-carbonitrile (20.7 g, 74.1%) as a brown solid which was used without further purification. LC-MS m/e calcd for $C_{12}H_{10}N_2O_3$ (MH⁺) 231. found 231.

The mixture of 6,7-dimethoxy-1-oxo-1,2-dihydro-isoquinoline-4-carbonitrile (8 g, 35 mmol) and phosphorus oxybromide (70 g, 244 mmol) in anisole (30 mL) was heated to 80° C. for 12 h. The solvent and excess POBr₃ were removed by rotary evaporator. The resulting solid was washed with hexane and dried. The solid was slowly added to ice and the product was extracted with chloroform. The organic layer was washed with saturated aqueous sodium carbonate solution, saturated aqueous sodium chloride solution (20 mL), dried over magnesium sulfate, filtered and concentrated in vacuo to afford a brown solid. Flash chromatography (Merck Silica gel 60, 70–230 mesh, methylenechloride) afforded 1-bromo-6,7-dimethoxy-isoquinoline-4-carbonitrile (7.5 g, 75%) as a brown solid. LC-MS m/e calcd for $C_{12}H_9BrN_2O_2$ (MH$^+$) 293. found 293.

Sodium hydride (11 mg, 0.26 mmol) was added to a stirred mixture of 1-bromo-6,7-dimethoxy-isoquinoline-4-carbonitrile (50 mg, 0.17 mmol), 2-naphthaldehyde (40.6 mg, 0.26 mmol), 1,3-dimethylimidazolium iodide (16 mg, 0.26 mmol) in DMF (2 mL). The reaction mixture became dark color. After 1 h, water (4 mL) was added to the above mixture, and extracted with chloroform (6 mL). The extract was washed with water (4 mL), dried over sodium sulfate, filtered and concentrated in vacuo to afford a solid which was used without further purification.

The mixture of above solid (0.17 mmol), sodium azide (34 mg, 0.51 mmol) and ammonium chloride (27 mg, 0.51 mmol) in DMF (2 mL) was stirred at 100° C. for 24 h. After removal of solvent, the crude product was purified directly by HPLC (Reverse C18, 10%–90% acetonitrile in water in 10 min) afforded our desired product as a solid. LC/MS m/e calcd for $C_{22}H_{16}N_6O_3$ (MH$^+$) 412. found 412.

EXAMPLE 2

[6,7-Dimethoxy-4-(1H-tetrazol-5-yl)-isoquinolin-1-yl]-quinolin-3-yl-methanone, trifluoroacetic acid salt

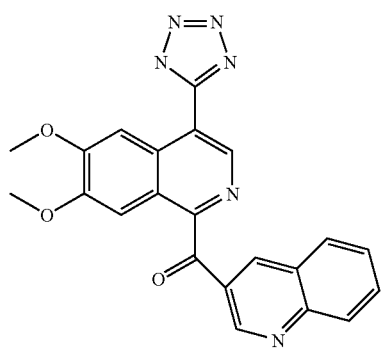

Similar to example 1 except that 3-quinolinecarboxaldehyde (0.26 mmol) was used instead of 2-naphthaldehyde (0.26 mmol) to afford the product as a solid. LC/MS m/e calcd for $C_{22}H_{16}N_6O_3$ (MH$^+$) 413. found 413.

EXAMPLE 3

[6,7-Dimethoxy-4-(1H-tetrazol-5-yl)-isoquinolin-1-yl]-(4-methoxy-naphthalen-1-yl)-methanone, trifluoroacetic acid salt

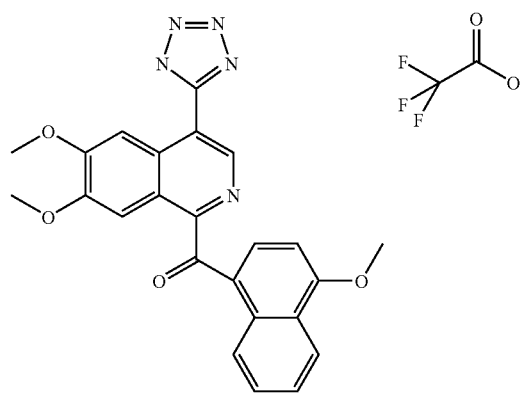

Similar to example 1 except that 4-methoxy-1-naphthaldehyde (0.26 mmol) was used instead of 2-naphthaldehyde (0.26 mmol) to afford the product as a solid. LC/MS m/e calcd for $C_{24}H_{19}N_5O_4$ (MH$^+$) 442. found 442.

EXAMPLE 4

[6,7-Dimethoxy-4-(1H-tetrazol-5-yl)-isoquinolin-1-yl]-(4-dimethylamino-naphthalen-1-yl)-methanone, trifluoroacetic acid salt

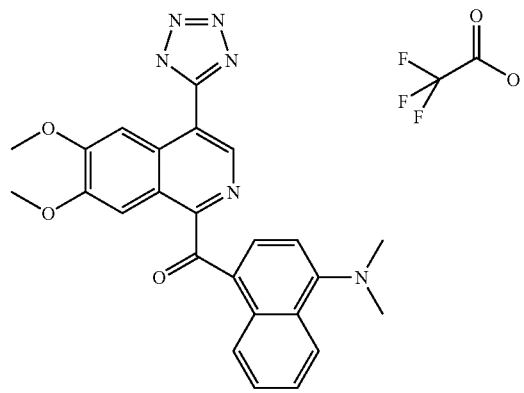

Similar to example 1 except that 4-dimethylamino-1-naphthaldehyde (0.26 mmol) was used instead of 2-naphthaldehyde (0.26 mmol) to afford the product as a solid. LC/MS m/e calcd for $C_{25}H_{22}N_6O_3$ (MH$^+$) 455. found 455.

EXAMPLE 5

(Naphthalen-1-yl)-[6,7-dimethoxy-4-(1H-tetrazol-5-yl)-isoquinolin-1-yl]-methanone, trifluoroacetic acid salt

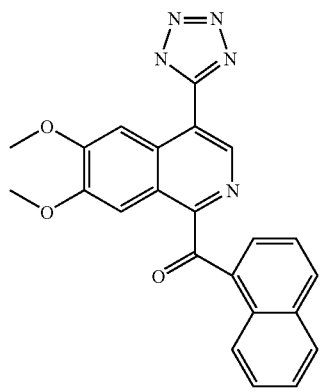
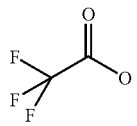

Similar to example 1 except that 1-naphthaldehyde (0.26 mmol) was used instead of 2-naphthaldehyde (0.26 mmol) to afford the product as a solid. LC/MS m/e calcd for $C_{23}H_{17}N_5O_3$ (MH$^+$) 412. found 412.

EXAMPLE 6

[6,7-Dimethoxy-4-(1H-tetrazol-5-yl)-isoquinolin-1-yl]-(4-methyl-naphthalen-1-yl)-methanone, trifluoroacetic acid salt

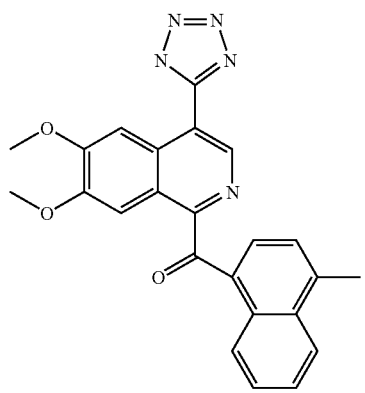
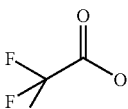

Similar to example 1 except that 4-methyl-1-naphthaldehyde (0.26 mmol) was used instead of 2-naphthaldehyde (0.26 mmol) to afford the product as a solid. LC/MS m/e calcd for $C_{24}H_{19}N_5O_3$ (MH$^+$) 426. found 426.

EXAMPLE 7

(2-Allyloxy-naphthalen-1-yl)-[6,7-dimethoxy-4-(1H-tetrazol-5-yl)-isoquinolin-1-yl]-methanone, trifluoroacetic acid salt

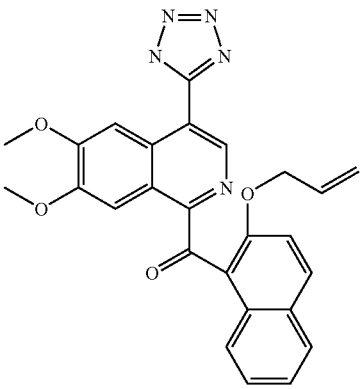
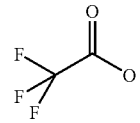

Similar to example 1 except that 2-allyloxy-1-naphthaldehyde (0.26 mmol) was used instead of 2-naphthaldehyde (0.26 mmol) to afford the product as a solid. LC/MS m/e calcd for $C_{26}H_{21}N_5O_4$ (MH$^+$) 468. found 468.

EXAMPLE 8

[6,7-Dimethoxy-4-(1H-tetrazol-5-yl)-isoquinolin-1-yl]-(7-methyl-naphthalen-2-yl)-methanone, trifluoroacetic acid salt

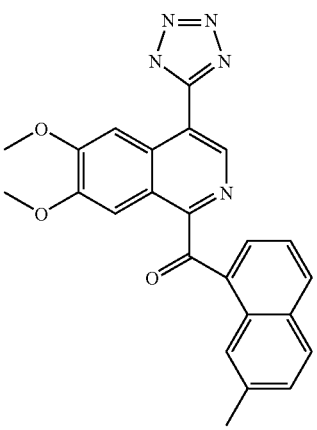
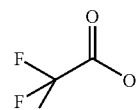

Similar to example 1 except that 7-methyl-2-naphthaldehyde (0.26 mmol) was used instead of 2-naphthaldehyde (0.26 mmol) to afford the product as a solid. LC/MS m/e calcd for $C_{24}H_{19}N_5O_3$ (MH$^+$) 426. found 426.

EXAMPLE 9

[6,7-Dimethoxy-4-(1H-tetrazol-5-yl)-isoquinolin-1-yl]-quinolin-8-yl-methanone, trifluoroacetic acid salt

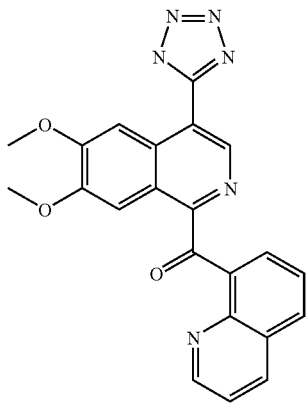
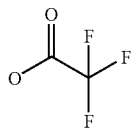

Similar to example 1 except that 8-quinolinecarboxaldehyde (0.26 mmol) was used instead of 2-naphthaldehyde (0.26 mmol) to afford the product as a solid. LC/MS m/e calcd for $C_{22}H_{16}N_6O_3$ (MH$^+$) 413. found 413.

EXAMPLE 10

[6,7-Dimethoxy-4-(1H-tetrazol-5-yl)-isoquinolin-1-yl]-(1,2,3,4-tetrahydro-phenanthren-9-yl)-methanone, trifluoroacetic acid salt

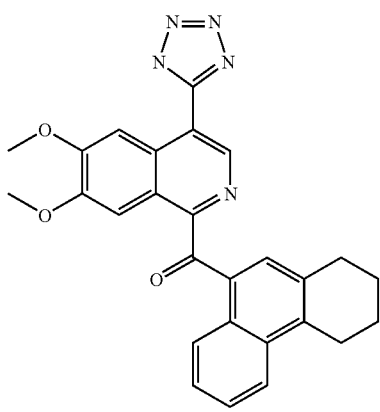
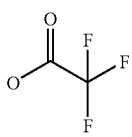

Similar to example 1 except that 9-(1,2,3,4-tetrahydro-phenanthrenecarboxaldehyde (0.26 mmol) was used instead of 2-naphthaldehyde (0.26 mmol) to afford the product as a solid. LC/MS m/e calcd for $C_{27}H_{23}N_5O_3$ (MH$^+$) 466. found 466.

EXAMPLE 11

[6,7-Dimethoxy-4-(1H-tetrazol-5-yl)-isoquinolin-1-yl]-(2-methoxy-naphthalen-1-yl)-methanone, trifluoroacetic acid salt

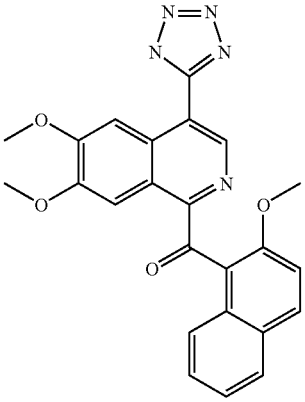
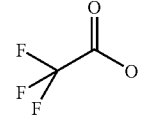

Similar to example 1 except that 2-methoxy-1-naphthaldehyde (0.26 mmol) was used instead of 2-naphthaldehyde (0.26 mmol) to afford the product as a solid. LC/MS m/e calcd for $C_{24}H_{19}N_5O_4$ (MH$^+$) 442. found 442.

EXAMPLE 12

1-(4-Dimethylamino-naphthalene-1-carbonyl)-6,7-dimethoxy-isoquinoline-4-carboxylic Acid, trifluoroacetic acid salt

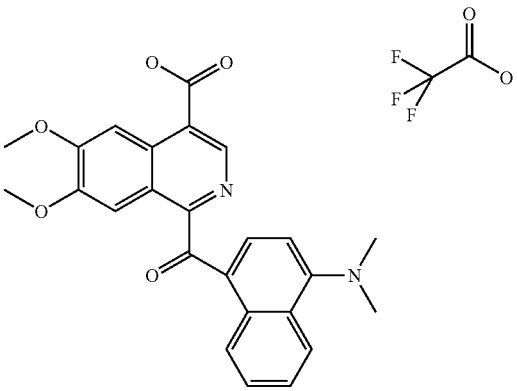

Sodium hydride (11 mg, 0.26 mmol) was added to a stirred mixture of 1-bromo-6,7-dimethoxy-isoquinoline-4-carbonitrile (see example 1) (50 mg, 0.17 mmol), 4-dimethylamino-1-naphthaldehyde (51.8 mg, 0.26 mmol), 1,3-dimethylimidazolium iodide (16 mg, 0.26 mmol) in DMF (2 mL). The reaction mixture became dark color. After 1 h, water (4 mL) was added to the above mixture, and extracted with chloroform (6 mL). The extract was washed with water (4 mL), dried over sodium sulfate, filtered and concentrated in vacuo to afford a solid. Flash chromatography (Merck Silica gel 60, 70-230 mesh, 0–40% EtOAc in methylenechloride in 30 min) afforded 1-(4-dimethylamino-naphthalene-1-carbonyl)-6,7-dimethoxy-isoquinoline-4-carbonitrile (31 mg, 41%) as a white solid. LC-MS m/e calcd for $C_{21}H_{18}N_2O_5$ (MH$^+$) 379. found 379.

To the suspension of 1-(4-dimethylamino-naphthalene-1-carbonyl)-6,7-dimethoxy-isoquinoline-4-carbonitrile (31 mg, 0.082 mmol) in methanol (2 mL) was added 25% of aqueous sodium hydroxide solution (0.27 mL, 1.68 mmol). The mixture was stirred at 90° C. for 12 h. After cooling to room temperature, the reaction was adjusted to pH=2 with 2 N HCl solution. The product was extracted with chloroform (2× 200 mL). The combined organic layers were washed with water (3×50 mL), dried over sodium sulfate, filtered, and concentrated in vacuo. The crude product was purified directly by HPLC (Reverse C18, 10%–90% acetonitrile in water in 10 min) afforded our desired product 1-(4-dimethylamino-naphthalene-1-carbonyl)-6,7-dimethoxy-isoquinoline-4-carboxylic acid (9 mg) as a solid. LC/MS m/e calcd for $C_{25}H_{22}N_2O_5$ (MH$^+$) 431. found 431.

EXAMPLE 13

1(4-methoxy-naphthalene-1-carbonyl)-6,7-dimethoxy-isoquinoline-4-carboxylic Acid, trifluoroacetic acid salt

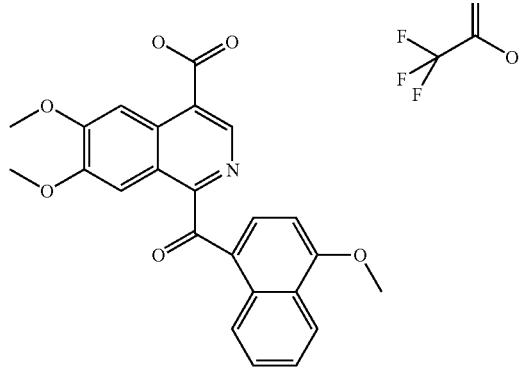

Similar to example 12 except that 4-methoxy-1-naphthaldehyde (0.26 mmol) was used instead of 4-dimethylamino-1-naphthaldehyde (0.26 mmol) to afford the product as a solid. LC/MS m/e calcd for $C_{24}H_{19}NO_6$ (MH$^+$) 418. found 418.

EXAMPLE 14

6,7-Dimethoxy-1-(1,2,3,4-tetrahydro-phenanthrene-9-carbonyl)-isoquinoline-4-carboxylic acid, trifluoroacetic acid salt

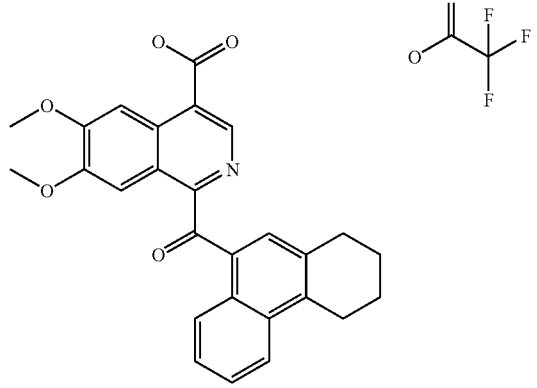

Similar to example 12 except that 9-(1,2,3,4-tetrahydro-phenanthrenecarboxaldehyde (0.26 mmol) was used instead of 4-dimethylamino-1-naphthaldehyde (0.26 mmol) to afford the product as a solid. LC/MS m/e calcd for $C_{27}H_{23}NO_5$ (MH$^+$) 442. found 442.

EXAMPLE 15

6,7-Dimethoxy-1-(naphthalene-1-carbonyl)-isoquinoline-4-carboxylic Acid

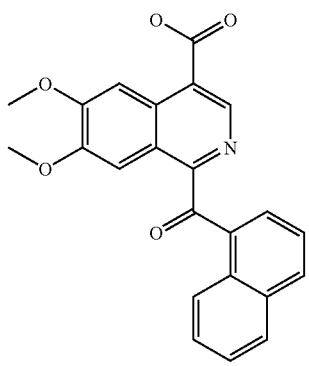

Similar to example 12 except that 1-naphthaldehyde (0.26 mmol) was used instead of 4-dimethylamino-1-naphthaldehyde (0.26 mmol) to afford the product as a solid. LC/MS m/e calcd for $C_{23}H_{17}NO_5$ (MH$^+$) 388. found 388.

EXAMPLE 16

In Vitro GFAT Assay

Enzyme Preparation:

COS cells transfected with GFAT-alpha or GFAT-beta, grown to 90% confluency were scraped into buffer containing PBS 100 mM, KCl 50 mM, EDTA 10 mM and protease inhibitors leupeptin, A-protinin, PMSF & pepstatin. The final concentration was $4 \times 10^{-7}$ cells/ml. This was sonicated with a microtip probe at setting 4 for 15 seconds on ice in a volume of 3–4 ml.

Incubation Buffer:

The buffer was prepared to contain: glutamine (8 mM, 0.01 ml), fructose 6-phosphate (100 mM, 0.01 ml), PBS 10×(0.01 ml), EDTA (50 mM, 0.01 ml), ±inhibitor (0.01 ml), enzyme (0.005 ml), and water (dilute to 0.10 ml).

Procedure:

The inhibitors are made up in 100% DMSO and diluted in a microtiter plate. The inhibitors were then added to the assay plate along with DMSO as a control. A reaction mixture was made, including enough for the standard curve samples, and kept on ice. The reaction was started by adding 90 ul of the mixture to the 96 well plate. The plate was covered with an adhesive plate sealer and placed in a 37° C. water bath for 60 minutes. Care was taken to ensure that no air bubbles form under the plate. After incubation, 10 ul of the glucosamine 6-phosphate standards made up in DMSO were added to the standard curve wells. A concentration range of 2.5 to 30 nmoles was in the linear part of the curve and covered the quantity of glucosamine 6-phosphate produced. The cold incubation mixture containing the enzyme was added to the control and standard curve wells. The glucosamine 6-phosphate was then acetylated by adding 10 ul of acetic anhydride 1.5% in acetone followed by 50 ul of potassium tetraborate (200 mM). The plate was sealed with a new cover and shaken for 2 minutes on a microshaker. The plate was placed in an 80° C. water bath for 25 minutes. The plate was then placed on ice for 5 minutes. 130 ul of Ehrlich's reagent was added to the wells and the plate placed in a 37° C. water bath for 20 minutes. The plate was then read at 585 nm. A softmax program has been set up to interpolate the ODs from the standard curve to give the nmoles produced.

The compounds of the present invention have GFAT inhibitory activity with IC50 below 100 μM.

What is claimed is:

1. A compound of formula (I):

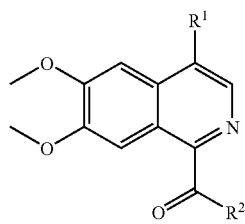

(I)

R$^1$ is —COOH, -lower alkyl-COOH, -lower alcohol, —CH$_2$OCH$_3$, —CH$_2$NH$_2$, —CH$_2$NHSO$_2$R$^7$, —C(=O)R$^8$, —CNHCH$_2$CH$_2$—R$^8$, —C(=NH)—R$^8$, —(CH$_2$)$_n$NHC(=O)R$^9$, —(CH$_2$)$_m$C(=O)N(R$^{11}$)(R$^{12}$), —C(=NH)—R$^{13}$, or —(CH$_2$)$_n$—R$^{14}$;

R$^2$ is

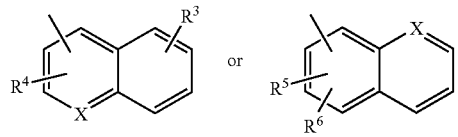

wherein

X is —CH or —N;

R$^3$, R$^4$, R$^5$, and R$^6$ are each selected from the group consisting of —H, -lower alkyl, —N(CH$_3$)$_2$, —N(CH$_3$)CH$_2$CH$_3$, —N(CH$_2$CH$_3$)CH$_2$CH$_3$, -halo, —O-lower alkene, -lower alkoxy, —O-lower alcohol, and —O(CH$_2$)$_n$-cycloalkyl; or where R$^5$ and R$^6$ are substituents on adjacent ring carbon atoms, optionally R$^5$ and R$^6$ together with the C atoms to which they are attached form a 5 or 6 membered saturated carbocyclic ring;

R$^7$ is —CF$_3$, -lower alkyl, —CH$_2$Cl, —CH$_2$CF$_3$, or —R$^8$;

R$^8$ is a 5 or 6 membered saturated substituted or unsubstituted heterocyclic ring containing one hetero atom which is selected from N, O, and S wherein the substituted ring is the heterocyclic ring substituted with —OH or -phenyl;

R$^9$ is -lower alkyl, -lower alkoxy, or —(CH$_2$)$_n$R$^{10}$;

R$^{10}$ is a 5 or 6 membered saturated or unsaturated heterocyclic ring containing one or two hetero atoms which are selected from N and O;

R$^{11}$ is —H or —CH$_3$;

R$^{12}$ is —H, -lower alkyl, —C≡N, —OH, -lower alkoxy, or —CH$_2$COOCH$_2$CH$_3$;

R$^{13}$ is -lower alkoxy, —NH$_2$ or —N-lower alkyl;

R$^{14}$ is a saturated or unsaturated 5 membered substituted or unsubstituted heterocyclic ring containing from 1 to 4 hetero atoms wherein the hetero atoms are selected from N, O and S, wherein the substituted ring is the heterocyclic ring which is substituted at one or two ring carbons with =O, or substituted at a ring N with -lower alcohol or -lower alkyl;

m is 0, 1 or 2;

n is 0 or 1;

or a pharmaceutically acceptable salt or ester thereof.

2. The compound according to claim 1, wherein R$^1$ is —COOH, lower alkyl-COOH, (CH$_2$)$_n$NHC(=O)R$^9$, —CH$_2$NHSO$_2$R$^7$, or —(CH$_2$)$_n$—R$^{14}$.

3. The compound according to claim 2, wherein R$^1$ is —COOH, -lower alkyl-COOH wherein -lower alkyl-COOH is —CH$_2$COOH, or —(CH$_2$)$_n$—R$^{14}$.

4. The compound according to claim 3, wherein R$^1$ is —COOH or —(CH$_2$)$_n$—R$^{14}$ and R$^{14}$ is an unsubstituted heterocyclic ring.

5. The compound according to claim 4, wherein R$^1$ is tetrazole.

6. The compound according to claim 2, wherein R$^1$ is —(CH$^2$)$_n$NHC(=O)R$^9$ or —CH$_2$NHSO$_2$R$^7$.

7. The compound according to claim 6, wherein R$^9$ is lower alkyl.

8. The compound according to claim 6, wherein R$^7$ is —CF$_3$.

9. The compound according to claim 1, wherein R$^2$ is

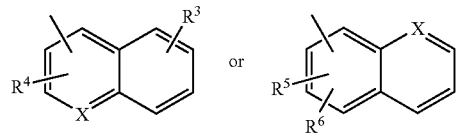

10. The compound according to claim 1, wherein X is is —CH.

11. The compound according to claim 1, wherein X is —N.

12. The compound according to claim 1, wherein R$^1$ is —(CH$_2$)$_n$R$^{14}$ wherein R$^{14}$ is an unsubstituted ring, —COOH, —CH$_2$COOH, -lower alcohol, —CH$_2$OCH$_3$, or —CH$_2$NH$_2$;

R$^2$ is

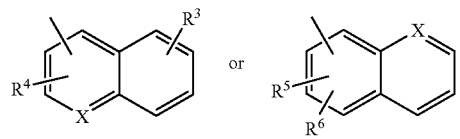

wherein

X is —CH or —N;

R$^3$, R$^4$, R$^5$, and R$^6$ are each selected from the group consisting of:

—H, -lower alkoxy,

—N(CH$_3$)CH$_3$,

-lower alkyl, and —O-lower alkene; or where R$^5$ and R$^6$ are substituents on adjacent ring carbon atoms, optionally R$^5$ and R$^6$ together with the C atoms to which they are attached form a 5 or 6 membered saturated carbocyclic ring.

13. The compound according to claim 1, wherein -lower alkyl is methyl, -lower alcohol is -methanol, -lower alkoxy is -methoxy, and -lower alkyl —COOH is —CH$_2$—COOH.

14. The compound according to claim 1, wherein R$^3$, R$^4$, R$^5$, and R$^6$ are each selected from the group consisting of:
—H, -lower alkyl which contains from 1 to 4 carbon atoms, —N(CH$_3$)$_2$, -lower alkoxy which contains from 1 to 4 carbon atoms, -halo, and —O-lower alkene which contains from 1 to 4 carbon atoms; or
where R$^5$ and R$^6$ are substituents on adjacent ring carbon atoms, optionally R$^5$ and R$^6$ together with the C atoms to which they are attached form a 6 membered saturated carbocyclic ring.

15. The compound according to claim 1, selected from the group consisting of:
(Naphthalen-2-yl)-[6,7-dimethoxy-4-(1H-tetrazol-5-yl)-isoquinolin-1-yl]-methanone, and
(Naphthalen-1-yl)-[6,7-dimethoxy-4-(1H-tetrazol-5-yl)-isoquinolin-1-yl]-methanone,
or a pharmaceutically acceptable salt thereof.

16. The compound according to claim 1, selected from the group consisting of:
[6,7-Dimethoxy-4-(1H-tetrazol-5-yl)-isoquinolin-1-yl]-quinolin-3-yl-methanone, and
[6,7-Dimethoxy-4-(1H-tetrazol-5-yl)-isoquinolin-1-yl]-quinolin-8-yl-methanone,
or a pharmaceutically acceptable salt thereof.

17. The compound according to claim 1, selected from the group consisting of:
[6,7-Dimethoxy-4-(1H-tetrazol-5-yl)-isoquinolin-1-yl]-(4-methoxy-naphthalen-1-yl)-methanone,
[6,7-Dimethoxy-4-(1H-tetrazol-5-yl)-isoquinolin-1-yl]-(4-dimethylamino-naphthalen-1-yl)-methanone.
[6,7-Dimethoxy-4-(1H-tetrazol-5-yl)-isoquinolin-1-yl]-(4-methyl-naphthalen-1-yl)-methanone,
(2-Allyloxy-naphthalen-1-yl)-[6,7-dimethoxy-4-(1H-tetrazol-5-yl)-isoquinolin-1-yl]-methanone,
[6,7-Dimethoxy-4-(1H-tetrazol-5-yl)-isoquinolin-1-yl]-(7-methyl-naphthalen-2-yl)-methanone,
[6,7-Dimethoxy-4-(1H-tetrazol-5-yl)-isoquinolin-1-yl]-(1,2,3,4-tetrahydro-phenanthren-9-yl)-methanone, and
[6,7-Dimethoxy-4-(1H-tetrazol-5-yl)-isoquinolin-1-yl]-(2-methoxy-naphthalen-1-yl)-methanone;
or a pharmaceutically acceptable salt thereof.

18. The compound according to claim 1, selected from the group consisting of:
1-(4-Dimethylamino-naphthalene-1-carbonyl)-6,7-dimethoxy-isoquinoline-4-carboxylic acid, and
1-(4-methoxy-naphthalene-1-carbonyl)-6,7-dimethoxy-isoquinoline-4-carboxylic acid, and
6,7-Dimethoxy-1-(1,2,3,4-tetrahydro-phenanthrene-9-carbonyl)-isoquinoline-4-carboxylic acid;
or a pharmaceutically acceptable salt thereof.

19. The compound according to claim 1, 6,7-Dimethoxy-1-(naphthalene-1-carbonyl)-isoquinoline-4-carboxylic acid, or a pharmaceutically acceptable salt thereof.

20. A pharmaceutical composition comprising a compound or a pharmaceutically acceptable salt thereof according to claim 1, and a pharmaceutically acceptable carrier.

21. A method for the treatment of type II diabetes in a patient in need of such treatment, comprising administering to the patient a therapeutically effective amount of a compound or a pharmaceutically acceptable salt thereof according to claim 1, in an amount of from about 10 mg to about 1,000 mg per day.

* * * * *